United States Patent
Rosenberg et al.

(10) Patent No.: US 9,828,643 B2
(45) Date of Patent: Nov. 28, 2017

(54) CHROMOSOME COPY NUMBER GAIN AS A BIOMARKER OF UROTHELIAL CARCINOMA LETHALITY

(75) Inventors: Jonathan E. Rosenberg, New York, NY (US); Joaquim Bellmunt, Barcelona (ES); Philip Kantoff, Brookline, MA (US); Massimo Loda, Belmont, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 9 days.

(21) Appl. No.: 13/475,432

(22) Filed: May 18, 2012

(65) Prior Publication Data

US 2012/0295807 A1    Nov. 22, 2012
US 2013/0165331 A9    Jun. 27, 2013

Related U.S. Application Data

(60) Provisional application No. 61/487,532, filed on May 18, 2011.

(51) Int. Cl.
    *C12Q 1/68*    (2006.01)
(52) U.S. Cl.
    CPC .......... *C12Q 1/6886* (2013.01); *C12Q 1/6851* (2013.01); *C12Q 2600/112* (2013.01)
(58) Field of Classification Search
    None
    See application file for complete search history.

(56) References Cited

U.S. PATENT DOCUMENTS

2008/0075722 A1*  3/2008  DePinho et al. ..... C12Q 1/6841
                                                     424/138.1
2009/0318533 A1  12/2009  Hu et al.

OTHER PUBLICATIONS

Eguchi et al., "The loss of 8p23.3 is a novel marker for predicting progression and recurrence of bladder tumors without muscle invasion," Cancer Genet. Cytogenet. 2010, 200:16-22, published online May 31, 2010.*
Beroukhim et al., The landscape of somatic copy-number alteration across human cancers. Nature. Feb. 18, 2010;463(7283):899-905.
Simon et al., Chromosomal aberrations associated with invasion in papillary superficial bladder cancer. J Pathol. Aug. 1998;185(4):345-51.
Vékony et al., Copy number gain at 8q12.1-q22.1 is associated with a malignant tumor phenotype in salivary gland myoepitheliomas. Genes Chromosomes Cancer. Feb. 2009;48(2):202-12.
International Preliminary Report on Patentability for PCT/US2012/038567 dated Nov. 28, 2013.

* cited by examiner

*Primary Examiner* — Kaijiang Zhang
(74) *Attorney, Agent, or Firm* — Wolf, Greenfield & Sacks, P.C.

(57) ABSTRACT

Diagnostic assays for medically classifying cancer patients are provided. The method comprises assessing a tissue sample of the patient for the presence of a copy number gain of chromosome regions 1q23.3 and/or 1q21.2. Copy number gain of chromosome regions 1q23.3 and/or 1q21.2 is indicative of a less favorable prognosis as compared to the prognosis if there was no copy number gain in the same regions.

16 Claims, 9 Drawing Sheets

CHROMOSOME COPY NUMBER GAIN AS A BIOMARKER OF UROTHELIAL CARCINOMA LETHALITY

RELATED APPLICATIONS

This application claims the benefit under 35 U.S.C. §119 (e) of U.S. provisional application Ser. No. 61/487,532, filed May 18, 2011, the content of which is incorporated by reference herein in its entirety.

BACKGROUND OF THE INVENTION

Current estimates from the American Cancer Society indicate that over 70,000 new cases of urothelial carcinoma (UC) are diagnosed annually in the US alone, and over 14,000 will die from the disease. While many patients' tumors recur in the urinary tract only, this relapsing non-invasive disease is usually not life-threatening. In contrast, other patients develop invasive and/or metastatic disease, the lethal phenotype of UC. While our understanding of the molecular changes in UC has rapidly evolved over the last few decades, the therapeutic arsenal has not. First-line treatment for advanced disease remains platinum-based combination chemotherapy, and no FDA-approved second-line treatment exists. Attempts to improve current therapies have focused on cytotoxic chemotherapy dose intensity and combination doublet and triplet regimens, none of which have led to substantial improvements in survival. Metastatic UC remains incurable in the vast majority of patients, with a median survival of approximately 8 months without treatment, and 14 months with treatment. Unlike treatment of other solid tumors, targeted therapies thus far have failed to advance the standard of care for UC. Furthermore, there is no clear molecular understanding of what defines the lethal phenotype of UC. Thus, there is an urgent need for new biomarkers and treatment approaches.

SUMMARY OF THE INVENTION

It has been discovered, surprisingly, that copy number gain of chromosome regions defined by chr 1:159256737-159407240 and/or chr 1:148747863-149235943 can predict poor prognosis in cancer. The invention involves obtaining a tissue sample of the subject, and determining from the tissue sample whether the subject has a copy number gain for a region of the subjects genome defined by chr 1:159256737-159407240 and/or chr 1:148747863-149235943. A copy number gain of the regions is indicative of a less favorable prognosis than the prognosis if there is no copy number gain.

According to one aspect of the invention, a copy number gain means determining a duplication of the entire or a portion of the genome regions defined by chr 1:159256737-159407240 and/or chr 1:148747863-149235943. In some embodiments, a copy number gain means determining a duplication of the entire or a portion of the genome regions defined by the genes located in the genome regions defined by chr 1:159256737-159407240 and/or chr 1:148747863-149235943. In some embodiments, the present invention involves determining whether the tissue sample from the subject has a copy number gain of any one or more of the genes located in the genome regions defined by chr 1:159256737-159407240, such as, JAM1, NIT1, PFDN2, PPOX, KAT, USF1, DEDD, DEDPR01, USP21, F11R, UFC1, PVRL4, KLHC9, ARHGAP30, TSTD1, FCGR and PBX1. In some embodiments, the present invention involves determining whether the tissue sample from the subject has a copy number gain of any one or more of the genes located in the genome regions defined by chr 1:148747863-149235943, such as, ARNT, CTSK, CTSS, ECM1, ENSA, MCL1, ANXA9, SETDB1, LASS2, ADAMTSL4, GOLPH3L, FAM63A, and HORMAD1.

In some embodiments, the method further comprises providing a report whether the subject has a copy number gain. In some embodiments, the method further comprises reporting prognostic information about the subject based on the existence or non-existence of copy number gain for the region. In some embodiments, the method further comprises providing information, based on the existence or non-existence of copy number gain of the region, that assists in medical care of the subject. The existence or non-existence of copy number gain for the region can optionally be reported to the subject.

In some embodiments, the less favorable prognosis may be (a) a higher risk of developing invasive/metastatic disease, (b) a higher risk of mortality within six (6) months, or (c) a higher risk of mortality within two (2) years. It is believed also that copy number gain may predict the likelihood that a subject may develop cancer.

In some embodiments, the tissue sample is cancerous. In some embodiments, the tissue sample is a bladder tissue sample. In some embodiments, the bladder tissue sample is cancerous.

According to some aspects of the invention, the determining step comprises hybridization. In some embodiments, the determining step comprises contacting DNA from the tissue sample with a probe. The probe could be a DNA probe, for example a PCR probe, an array of DNA on a chip or a labeled DNA probe, such as a fluorescently labeled DNA probe. The probe hybridizes to at least part of the genome region defined by chr 1:159256737-159407240 and/or chr 1:148747863-149235943.

The subject (individual) is a human. In some embodiments, the subject is known to have urinary cancer, or invasive or metastatic urinary cancer.

These and other aspects of the inventions, as well as various advantages and utilities will be apparent with reference to the Detailed Description. Each aspect of the invention can encompass various embodiments as will be understood.

BRIEF DESCRIPTION OF THE DRAWINGS

FIG. 2 shows recurrent copy number gains (2A) and losses (2B) in the Spanish cohort of UC patients as well as recurrent copy number gains (2C) and losses (2D) in the BW/DF cohort of UC patients.

FIG. 3 demonstrates the prognostic utility of 1q23.3 amplification. The figure shows the Kaplan-Meier plots for the Spanish cohort (FIG. 3A; aCGH), BW/DF cohort (FIG. 3B, SNP array), and BW/DF and Greek cohorts (FIG. 3C, FISH) stratified by the 1q23.3 amplification.

DETAILED DESCRIPTION OF THE INVENTION

The present invention, in one aspect, relates to the surprising discovery that copy number gain of particular regions of chromosomes is associated with poor clinical outcomes. In particular, the invention is based on the identification of the association between copy number gain of chromosome regions 1q23.3 and 1q21.2 with a poor prognosis in UC. While previous work has identified 1q23.3 as gained in UC, and in other malignancies, this previous work did not make any association between copy number findings and clinical outcomes. As is common in medicine, markers are discoveries which are shown to be present in some portion of subjects with a disease. The presence of the marker, however, is not established as having any predictive value as to whether a disease will develop in the first instance (should the marker be present prior to development of the disease) or how the disease will progress (should the disease already be present. Instead, until it is proven otherwise, such markers may be assumed to result from the disease.

According to one aspect, the present invention provides diagnostic assays for medically classifying cancer patients which comprises assessing a tissue sample of the patient for the presence of a copy number gain of chromosome regions 1q23.3 and/or 1q21.2. Copy number gain of chromosome regions 1q23.3 and/or 1q21.2 is indicative of a less favorable prognosis as compared to the prognosis if there was no copy number gain in the same regions.

The tissue sample can be any tissue sample from which a copy number gain can be determined. In some embodiments, the tissue sample can be obtained from a local solid tumor or suspected tumor, or tumor resulting from metastasis. Non-limiting examples of tissue samples include tumor samples obtained from bladder cancer, urothelial carcinoma, small cell carcinoma, squamous carcinoma, adenocarcinoma, leiomyosarcoma (a tumor arising from smooth muscle), lymphoma (a tumor that usually arises in the lymph nodes), malignant melanoma (a tumor that usually arises from the skin) breast cancer, cervical cancer, colon cancer (including colorectal cancer), esophageal cancer, gastric cancer, head and neck cancer, liver cancer, lung cancer (both small cell and non-small cell), melanoma, myeloma, neuroblastoma, ovarian cancer, pancreatic cancer, prostate cancer, renal cancer, sarcoma (including osteosarcoma), skin cancer (including squamous cell carcinoma), stomach cancer, testicular cancer, thyroid cancer, and uterine cancer. In important embodiments, the tissue sample comprises a bladder sample of the patient.

The tissue sample may be a fresh frozen tissue sample, or a paraffin-embedded tissue sample. The tissue can be genomic tissue, extra-nuclear tissue (e.g., tissue containing mRNA), or can be isolated from blood (i.e. tumor tissue resulting from metastasis). The copy number gain can be determined in the genome itself (i.e. the location where the copy exists), or the copy number gain can be determined indirectly. For example, copy number is sometimes associated with increased levels of mRNA, protein expression or activity. Thus, copy number gain may be determined from tissues containing the indirect measure. Non-limiting examples of such tissue samples include urine sample, blood sample, bone marrow sample, lymph node sample, and spinal fluid sample.

According to one aspect of the invention, a tissue sample obtained from the patient is analyzed. To practice the invention as claimed, it is not necessary for the person determining the copy number gain to obtain the tissue sample directly from the subject. In some embodiments, the tissue sample may be removed from the subject by a medical practitioner (e.g., a doctor, nurse, or a clinical laboratory practitioner), and then provided to the person determining the copy number gain. The tissue sample may be provided to the person determining the copy number gain by the subject or by a medical practitioner (e.g., a doctor, nurse, or a clinical laboratory practitioner). In some embodiments, the person determining the copy number gain obtains a tissue sample from the subject by removing the sample from the subject.

As used herein, a copy number gain means determining a duplication of the entire or a portion of the genome regions defined by chr 1:159256737-159407240 and/or chr1:148747863-149235943. In some embodiments, a copy number gain means determining a duplication of the entire or a portion of the genome regions defined by the genes located in the genome regions defined by chr 1:159256737-159407240 and/or chr1:148747863-149235943. In some embodiments, a copy number gain means determining a duplication of any one or more of the genes located in the genome regions defined by chr 1:159256737-159407240 and/or chr1:148747863-149235943. Thus, in some embodiments, the present invention involves determining whether the tissue sample from the subject has a copy number gain of any one or more of the genes located in the genome regions defined by chr 1:159256737-159407240, such as, JAM1, NIT1, PFDN2, PPOX, KAT, USF1, DEDD, DEDPR01, USP21, F11R, UFC1, PVRL4, KLHC9, ARHGAP30, TSTD1, FCGR and PBX1. In some embodiments, the present invention involves determining whether the tissue sample from the subject has a copy number gain of any one or more of the genes located in the genome regions defined by chr1:148747863-149235943, such as, ARNT, CTSK, CTSS, ECM1, ENSA, MCL1, ANXA9, SETDB1, LASS2, ADAMTSL4, GOLPH3L, FAM63A, and HORMAD1.

Methods of determining the copy number gain of a particular genomic region are well known in the art, and include, hybridization and amplification based assays. According to the methods of the invention, DNA copy number gains may be identified using copy number profiling, such as comparative genomic hybridization (CGH) (including both dual channel hybridization profiling and single channel hybridization profiling (e.g. SNP-CGH)). Other suitable methods including fluorescent in situ hybridization (FISH), PCR, nucleic acid sequencing, and Southern blot analysis may be used in accordance with the invention.

In some embodiments of the invention, the DNA copy number gains are identified using CGH. In comparative genomic hybridization methods, a "test" collection of nucleic acids (e.g. from a tumor or cancerous cells) is labeled with a first label, while a second collection (e.g. from a normal cell or tissue) is labeled with a second label. The ratio of hybridization of the nucleic acids is determined by the ratio of the first and second labels binding to each fiber in an array. Differences in the ratio of the signals from the two labels, for example, due to gene amplification in the test collection, is detected and the ratio provides a measure of the gene copy number, corresponding to the specific probe used. A cytogenetic representation of DNA copy-number variation can be generated by CGH, which provides fluorescence ratios along the length of chromosomes from differentially labeled test and reference genomic DNAs.

In some embodiments of the present invention, the DNA copy number gains are analyzed by microarray based CGH (array-CGH). Microarray technology offers high resolution. For example, the traditional CGH generally has a 20 Mb limited mapping resolution; whereas in microarray based CGH, the fluorescence ratios of the differentially labeled test and reference genomic DNAs provide a locus-by-locus measure of DNA copy-number variation, thereby achieving increased mapping resolution. Details of various microarray methods can be found in the literature. See, for example, U.S. Pat. No. 6,232,068; Pollack et al., Nat. Genet., 23(1): 41-6, (1999), Pastinen (1997) Genome Res. 7: 606614; Jackson (1996) Nature Biotechnology 14:1685; Chee (1995) Science 274: 610; WO 96/17958, Pinkel et al. (1998) Nature Genetics 20: 207-211 and others. High resolution CGH arrays can be performed using the Agilent or Affymetrix platforms. The DNA used to prepare the CGH arrays is not critical. For example, the arrays can include genomic DNA, e.g., overlapping clones that provide a high resolution scan of the portion of the genome of interest.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other suitable methods include are the nucleic acid sequence based amplification (NASBAO, Cangene, Mississauga, Ontario) and Q Beta Replicase systems. In one embodiment of the invention, the DNA copy number alterations in a genome are determined by single channel profiling, such as single nucleotide polymorphism (SNP)-CGH. Traditional CGH data consists of two channel intensity data corresponding to the two alleles. The comparison of normalized intensities between a reference and subject sample is the foundation of traditional array-CGH. Single channel profiling (such as SNP-CGH) is different in that a combination of two genotyping parameters are analyzed: normalized intensity measurement and allelic ratio. Collectively, these parameters provide a more sensitive and precise profile of chromosomal aberrations. SNP-CGH also provides genetic information (haplotypes) of the locus undergoing aberration.

In some embodiments, NanoString direct DNA and/or mRNA quantification is used to determine the copy number gain (Nat Biotechnol. 2008 March; 26(3):293-4). NanoString technology requires less DNA as compared to CGH-array, and allows precise measurement of copy number gain.

In some embodiments, the Panomics CNV DNA service may be used to determine the copy number gain.

In another embodiment, FISH is used to determine the DNA copy number alterations in a genome. Fluorescence in situ hybridization (FISH) is known to those of skill in the art (see Angerer, 1987 Meth. Enzymol., 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments.

In a typical in situ hybridization assay, cells or tissue sections are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions.

In some applications it is necessary to block the hybridization capacity of repetitive sequences. Thus, in some embodiments, tRNA, human genomic DNA, or Cot-1 DNA is used to block non-specific hybridization.

In another embodiment, Southern blotting is used to determine the DNA copy number alterations in a genome. Methods for doing Southern blotting are known to those of skill in the art (see Current Protocols in Molecular Biology, Chapter 19, Ausubel, et al., Eds., Greene Publishing and Wiley-Interscience, New York, 1995, or Sambrook et al., Molecular Cloning: A Laboratory Manual, 2d Ed. vol. 1-3, Cold Spring Harbor Press, NY, 1989). In such an assay, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., genomic DNA from the same or related cell, tissue, organ, etc.) provides an estimate of the relative copy number of the target nucleic acid.

In one embodiment, amplification-based assays, such as PCR, are used to determine the DNA copy number alterations in a genome. In such amplification-based assays, the genomic region where a copy number alteration occurred serves as a template in an amplification reaction. In a quantitative amplification, the amount of amplification product will be proportional to the amount of template in the original sample. Comparison to appropriate controls provides a measure of the copy number of the genomic region. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided, for example, in Innis et al. (1990) PCR Protocols, A Guide to Methods and Applications, Academic Press, Inc. N.Y.

Real time PCR can be used in the methods of the invention to determine DNA copy number alterations. (See, e.g., Gibson et al., Genome Research 6:995-1001, 1996; Heid et al., Genome Research 6:986-994, 1996). Real-time PCR evaluates the level of PCR product accumulation during amplification. To measure DNA copy number, total genomic DNA is isolated from a sample. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif.). To quantify the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from 10-106 copies of the gene of interest are generally sufficient. In addition, a standard curve is generated for the control sequence. This permits standardization of initial content of the nucleic acid of interest in a tissue sample to the amount of control for comparison purposes.

Methods of real-time quantitative PCR using TaqMan probes are well known in the art. Detailed protocols for real-time quantitative PCR are provided, for example, for RNA in: Gibson et al., 1996, A novel method for real time quantitative RT-PCR. Genome Res., 10:995-1001; and for DNA in: Heid et al., 1996, Real time quantitative PCR. Genome Res., 10:986-994.

A TaqMan-based assay also can be used to quantify a particular genomic region for DNA copy number alterations. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe.

This cleavage separates the 5' fluorescent dye and the 3' quenching agent, thereby resulting in an increase in fluorescence as a function of amplification.

Other suitable amplification methods include, but are not limited to ligase chain reaction (LCR) (see Wu and Wallace (1989) Genomics 4:560, Landegren et al. (1988) Science 241:1077, and Barringer et al. (1990) Gene 89:117), transcription amplification (Kwoh et al. (1989) Proc. Natl. Acad. Sci. USA 86:1173), self-sustained sequence replication (Guatelli et al. (1990) Proc. Nat. Acad. Sci. USA 87:1874), dot PCR, and linker adapter PCR, etc. In one embodiment, DNA sequencing is used to determine the DNA copy number alterations in a genome. Methods for DNA sequencing are known to those of skill in the art.

In one embodiment, karyotyping (such as spectral karyotyping, SKY) is used to determine the chromosomal structural aberrations in a genome. Methods for karyotyping are known to those of skill in the art. For example, for SKY, a collection of DNA probes, each complementary to a unique region of one chromosome, may be prepared and labeled with a fluorescent color that is designated for a specific chromosome. DNA amplification, translocations or other structural abnormalities may be determined based on fluorescence emission of the probes.

Copy number gain is sometimes associated with a mutation leading to increased levels of mRNA, protein expression or activity. In some embodiments, DNA copy number gain is determined by quantifying the increase in the levels of mRNA or protein expression and activity. mRNA levels can be measured using methods well known in the art, such as Northern blot analysis, and real time PCR. Protein levels can be measured using standard protein assays, using immunologic-based assays (such as ELISAs and related techniques), or using activity assays.

As used herein, the term prognosis refers to a prediction of the probable outcome of a medical condition, such as cancer. In the case of the present invention, the prognosis is typically performed based on the gain in copy number of all or part of the genome regions defined by chr 1:159256737-159407240 and/or chr 1:148747863-149235943. Suitably, the prognosis may be favorable, i.e. the absence of copy number gain reflects an improved prognosis of the cancer indicating that the subject is at a lower risk of developing invasive/metastatic disease, or has a lower risk of mortality within six months or two years. Alternatively, the presence of copy number gain may reflect that the prognosis is less favorable (i.e. the subject is at a higher risk of developing invasive/metastatic disease, or has a higher risk of mortality within six months or two years).

A report summarizing the results of the analysis, i.e. the presence or absence of the copy number gain in the subject's genome and any other information pertaining to the analysis could optionally be generated as part of the analysis (which may be interchangeably referred to herein as "providing" a report, "producing" a report, or "generating" a report). Examples of reports may include, but are not limited to, reports in paper (such as computer-generated printouts of test results) or equivalent formats and reports stored on computer readable medium (such as a CD, computer hard drive, or computer network server, etc.). Reports, particularly those stored on computer readable medium, can be part of a database (such as a database of patient records, which may be a "secure database" that has security features that limit access to the report, such as to allow only the patient and the patient's medical practitioners to view the report, for example). In addition to, or as an alternative to, generating a tangible report, reports can also be displayed on a computer screen (or the display of another electronic device or instrument).

A report can further be transmitted, communicated or reported (these terms may be used herein interchangeably), such as to the individual who was tested, a medical practitioner (e.g., a doctor, nurse, clinical laboratory practitioner, genetic counselor, etc.), a healthcare organization, a clinical laboratory, and/or any other party intended to view or possess the report. The act of 'transmitting' or 'communicating' a report can be by any means known in the art, based on the form of the report. Furthermore, "transmitting" or "communicating" a report can include delivering a report ("pushing") and/or retrieving ("pulling") a report. For example, reports can be transmitted/communicated by such means as being physically transferred between parties (such as for reports in paper format), such as by being physically delivered from one party to another, or by being transmitted electronically or in signal form (e.g., via e-mail or over the internet, by facsimile, and/or by any wired or wireless communication methods known in the art), such as by being retrieved from a database stored on a computer network server, etc.

As used herein, the term "reporting prognostic information" refers to providing information regarding the impact of the presence of cancer (e.g., as determined by the diagnostic methods of the present invention) on a subject's future health (e.g., expected morbidity or mortality, the likelihood of getting cancer or, and the risk of metastasis) based on the existence or non-existence of copy number gain of the region. This information may assist in the medical care of the subject. Medical care as defined herein includes both medical diagnosis and therapeutic treatment of the subject. For example, the copy number gain can identify subjects who are destined to develop invasive and/or metastatic cancer, and who, therefore, require aggressive therapy.

The present invention is further illustrated by the following Example, which in no way should be construed as further limiting. The entire contents of all of the references

EXAMPLES

Materials and Methods

Patients: Three cohorts of patients were identified for this study. To be eligible, all patients had to have developed metastatic UC, and have primary tumor tissue available for analysis. All specimens were formalin-fixed and paraffin embedded from three sources: Spain (primary tumors from patients who developed metastatic disease), Greece (HECOG specimens from an aborted phase III study of dose-dense gemcitabine and cisplatin or dose-dense M-VAC chemotherapy), and Dana-Farber/Brigham and Women's Cancer Center. Slides were evaluated and tumor-bearing 0.6 mm cores were punched for DNA extraction by standard methodology and/or tissue microarray (TMA) construction. All cases were collected under IRB approved protocols at the different institutions, de-identified, and approved for use via an exemption by the Dana-Farber/Harvard Cancer Center institutional review board.

Spanish Cohort. All patients in this cohort were treated for metastatic disease with platinum-based cytotoxic chemotherapy. Median overall survival for this cohort was 15 months. DNA was hybridized to Agilent Oligonucleotide human genome 180 k array CGH arrays. Normal male 46, XY genomic DNA was obtained from Promega (Madison, Wis.). Genomic DNA was extracted using the QIAamp DNA FFPE Tissue Kit (Qiagen, Valencia, Calif.). The Genomic DNA ULS labeling kit for FFPE Samples (Agilent) was used to chemically label 500 ng of genomic DNA with either ULS-Cy5 (tumor) or ULS-Cy3 dye (normal/reference DNA) according to the manufacturer's protocol (AgilentTechnologies, Inc., Palo Alto, Calif.). Samples were hybridized to the Agilent SurePrint G3 Human CGH+SNP Microarray 4×180K. Each slide contains four identical arrays consisting of approximately 170,334 in situ synthesized 60-mer oligonucleotide probes that span coding and non-coding sequences with an average spatial resolution of 13 kb. The sample was applied to the array using an Agilent microarray hybridization chamber and hybridization was carried out for 40 hours at 65° C. in a Robbins Scientific rotating oven at 20 rpm. The arrays were then disassembled according to the manufacturer's protocol. Slides were dried and scanned using an Agilent DNA microarray scanner. CGH Analytics software version 3.4 (Agilent Technologies, Calif.) was used to analyze the aCGH data.

BW/DF Cohort. We obtained data on n=47 patients from the Dana-Farber/Harvard Cancer Center. All patients in this cohort went on to develop metastatic disease and had primary tumor tissue available. DNA was hybridized to Affymetrix OncoScan™ FFPE Express 2.0 SNP molecular inversion probe arrays with 334,183 copy number and SNP probes. Median probe spacing was 9 kb. Matched normals were available for 41 samples. Copy numbers were estimated with the NEXUS software. Quality control was carried out by Affymetrix and only samples that passed their metrics (MAPD value of ≤0.6) were considered. A tissue microarray was stained with a FISH probe targeting the region of 1q23.3 identified in the Spanish cohort, and was scored for copy number gain or amplification in 33 patients from the BW/DF cohort by a single.

Greek Cohort. We obtained data on n=93 patients from an unfinished randomized phase III study from Greece. Patients all had metastatic UC and ECOG performance status (PS) 0 or 1, and a majority was randomized to either dose-dense MVAC or dose-dense Gem-Cis. After randomization was stopped, additional patients received dose-dense MVAC; this group of patients was also included in the cohort. Patients with ECOG PS 0-2 were included in this latter group. Overall survival for this cohort of patients was 16 months. A tissue microarray was stained with a FISH probe targeting the region of 1q23.3 identified in the Spanish cohort, and was scored for copy number gain or amplification in all patients from the Greek cohort by a single cytogeneticist (AL).

TCGA Cohort. We further obtained copy number data from The Cancer Genome Atlas (TCGA). We acquired segmented data from the TCGA bladder cancer cohort (n=35), and the TCGA primary glioblastoma (GBM) cohort (n=518).

Clinical Endpoints: The primary endpoint was overall survival (OS) from the start of front-line chemotherapy for detection of metastatic disease in the Spanish cohort. For the BW/DF cohort, overall survival was defined as starting from the diagnosis date of metastatic recurrence, due to the unavailability of initial treatment dates in this cohort for most patients. For the Greek cohort and all 33 BW/DF patients that were tested using FISH, treatment dates were available and the primary endpoint in the FISH study was the overall survival from the start of chemotherapy.

Recurrent Copy Number Aberrations. Normalized copy number data was first segmented using GLAD with default parameters as available in GenePattern version 3.3.3. The Genomic Identification of Significant Targets in Cancer (GISTIC) software (v2.0.12) was then used to identify regions of the genome that were significantly amplified or deleted across a set of samples. Each region was assigned a score that considers the amplitude of the region as well as the frequency of its occurrence across samples. The software estimated false discovery rates (q-values) as well as potential targets (drivers) of the aberrations. For the latter, a "wide peak" region was determined that contained the target with a specified confidence level. We used GISTIC with a confidence level of 0.95 and otherwise default parameters. Copy number alterations were defined as broad if more than 50% of a chromosome arm was lost or gained, otherwise as focal. Copy numbers of the altered regions as reported by GISTIC corresponded to the maximum copy numbers within the wide peak regions. To compare the GISTIC results of our bladder cancer specimens with findings from other cancer types, we extracted q-values from wide peak regions determined in a pooled analysis of 3,131 TCGA specimens from 26 histologic types.

Survival analysis. Copy numbers of significantly amplified or deleted regions (q-value<0.25) were dichotomized based on the standard GISTIC cutoffs for amplifications or deletion (log base 2 ratio>0.9 or <−1.3, respectively). Cox proportional hazard models were then used to assess the associations of these regions and overall survival. Cox p-values were adjusted for multiple comparisons using the Benjamini and Hochberg method. Association of 1q23.3 amplification and overall survival was further adjusted for ECOG performance status (>0) and visceral metastasis.
Results

Example 1

Figure 1:
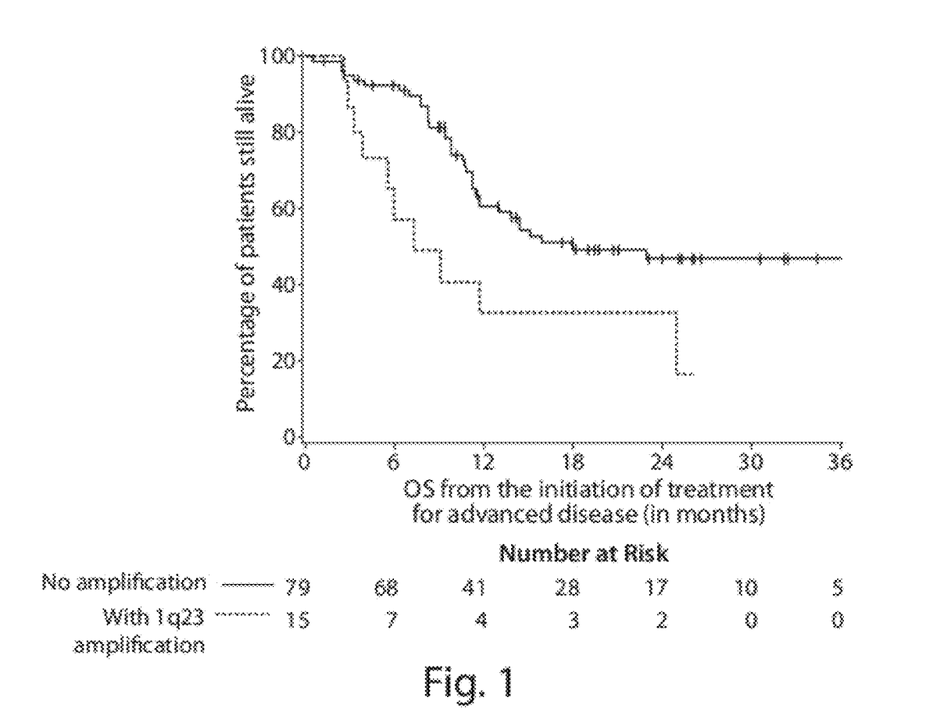
FIG. 1 shows that gain of the 150 kb region of 1q23.3 was significantly associated with lethal bladder cancer.

A cohort of 94 patients was identified. These patients all developed metastatic UC, the lethal phenotype of this cancer for which they subsequently received platinum-based combination chemotherapy. Clinical data was tabulated in collaboration with the study biostatistician. Overall survival data, defined as the time from start of chemotherapy for metastatic disease, was collected on these patients (Discovery cohort, Table 1). Tumor-bearing formalin-fixed, paraffin embedded (FFPE) tissue blocks from transurethral resection (TUR) or cystectomy specimens were evaluated by a single UC pathologist to identify malignant tissue. Multiple 0.6 mm cores were taken from tumor tissue and genomic DNA and total RNA was extracted. Tissue microarrays were also constructed from this cohort. Using the genomic DNA, high resolution CGH arrays were performed using Agilent 4×180 k chips with an average resolution of 13 kb to assess copy number alterations. Gain and Loss Analysis of DNA (GLAD) 16 was used to segment the array output, and Genomic Identification of Significant Targets in Cancer (GISTIC) v217 was used to assess the significance of gains and losses. Thresholds for gain and loss were set at log base 2 as greater than 0.9 and less than −1.3, respectively. It is critical to note that the aCGH experiments were done without knowledge of survival (i.e. when initially calling a gain or loss). False discovery rates (FDR) less than 0.2 were considered significant. In univariate analysis, copy number gain of 1q23.3 was significantly associated with poor survival (HR 2.4 for death, p=0.01, FDR=0.12). These data were then evaluated in a multivariable Cox model for survival controlling for known prognostic variables such as performance status and visceral metastasis, and confirmed with bootstrap analysis (500 resamplings). Gain of the 150 kb region of 1q23.3 was significantly associated with lethal bladder cancer (HR 2.94 for death, p=0.007) (FIG. 1 and Table 2). Bootstrapping (500 re-samples) internally validated the findings (HR=3.2, 95% CI 1.25-7.2). Of note, the minimum gained region is not known to contain significant germline copy number variants that span the 150 kb region (UCSC Genome Browser). The exact chromosome locus is chr 1:159256737-159407240 in human genome build 18. Very similar results are noted for a nearby but distinct region at 1q21.2 (chr 1:148747863-149235943), which is independently prognostic for outcome.

TABLE 1

|  | Discovery (n = 94) | |
| --- | --- | --- |
| ECOG PS | N | % |
| 0 | 34 | 36% |
| 1 | 58 | 62% |
| 2 | 2 | 2% |
| 3 | — | — |
| Missing | — | — |
| Visceral metastasis | 33 | 35% |
| Number of deaths | 46 | 49% |

TABLE 2

|  | HR (95% CI) | p-value |
| --- | --- | --- |
| 1q23.3 gain (yes vs. no) | 2.94 (1.35, 6.44) | 0.007 |
| ECOG PS (1, 2 vs. 0) | 1.93 (1.00, 3.79) | 0.05 |
| Visceral Disease (yes vs. no) | 2.40 (1.25, 4.47) | 0.008 |

Example 2

Median overall survival for the Spanish aCGH, Greek FISH, BW/DF FISH, and BW/DF MIP are 15.1, 18.0, 12.2 and 10.5 months, respectively, and median follow-up for these cohorts was 23.1, 50.1, 131, and 60.9 months. There were significant differences between the cohorts in the percentage of patients with visceral metastases and poor performance status. Table 3 summarizes patient characteristics in all three cohorts.

Figure 2A:
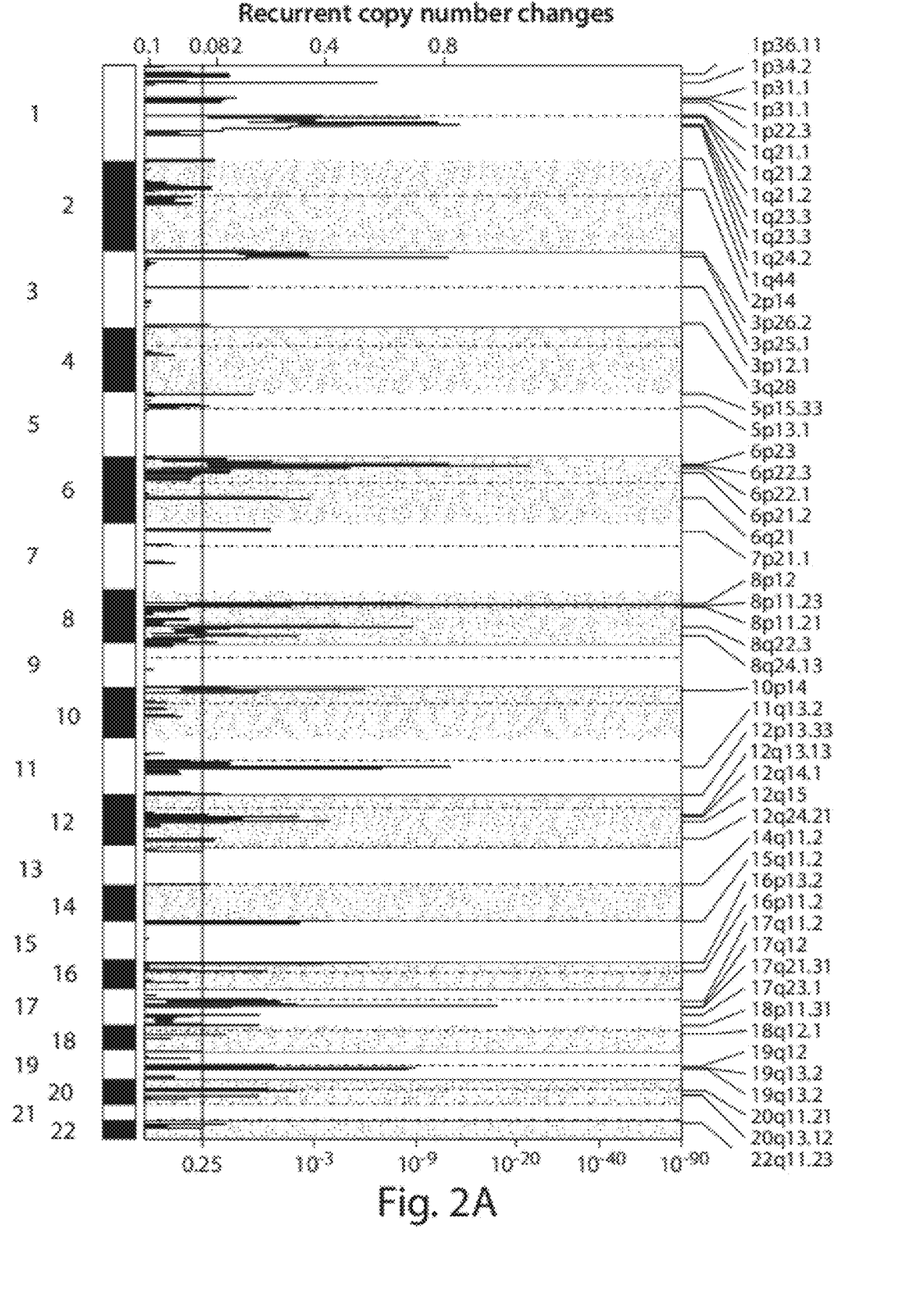
Figure 2B:
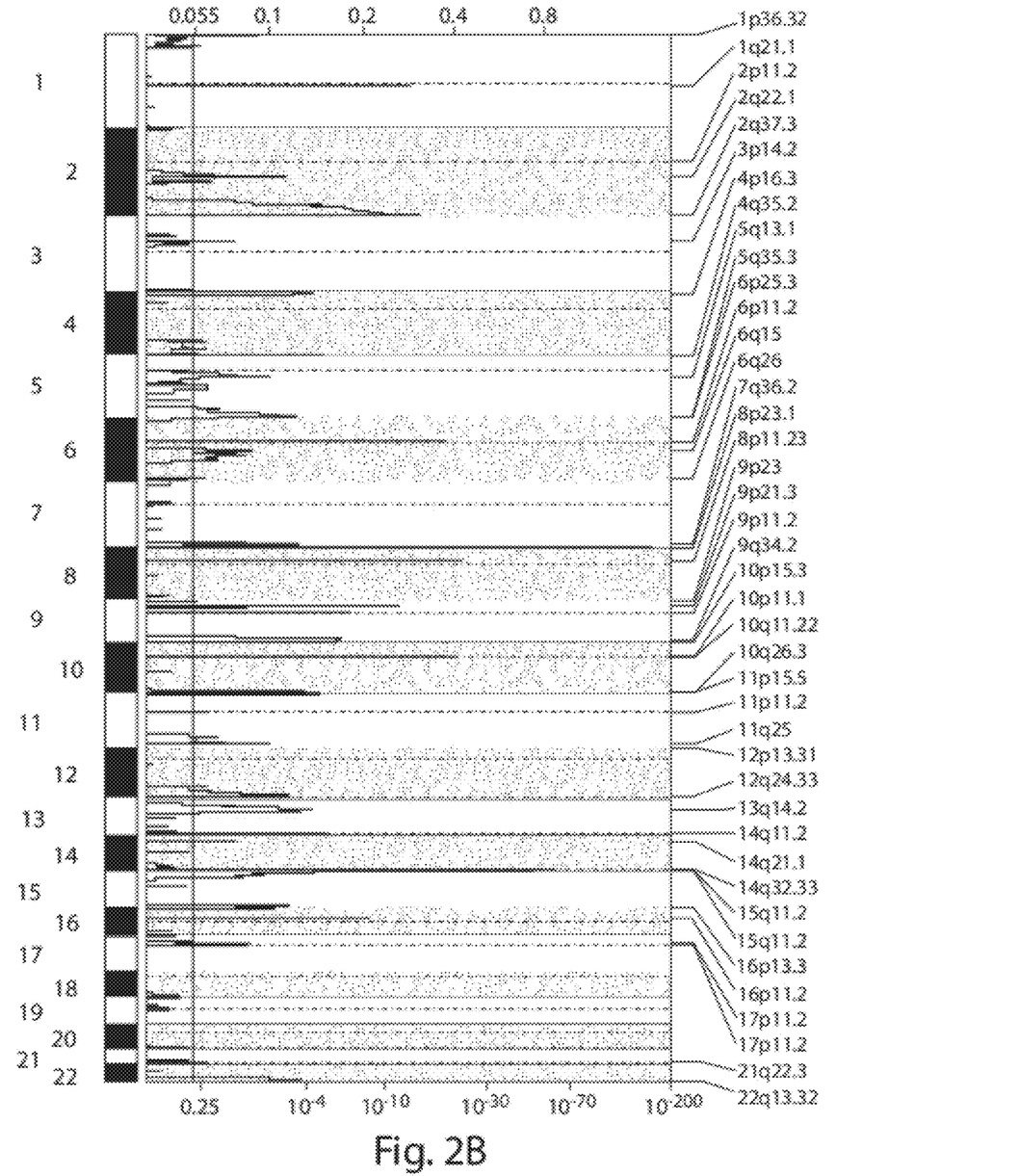
Figure 2C:
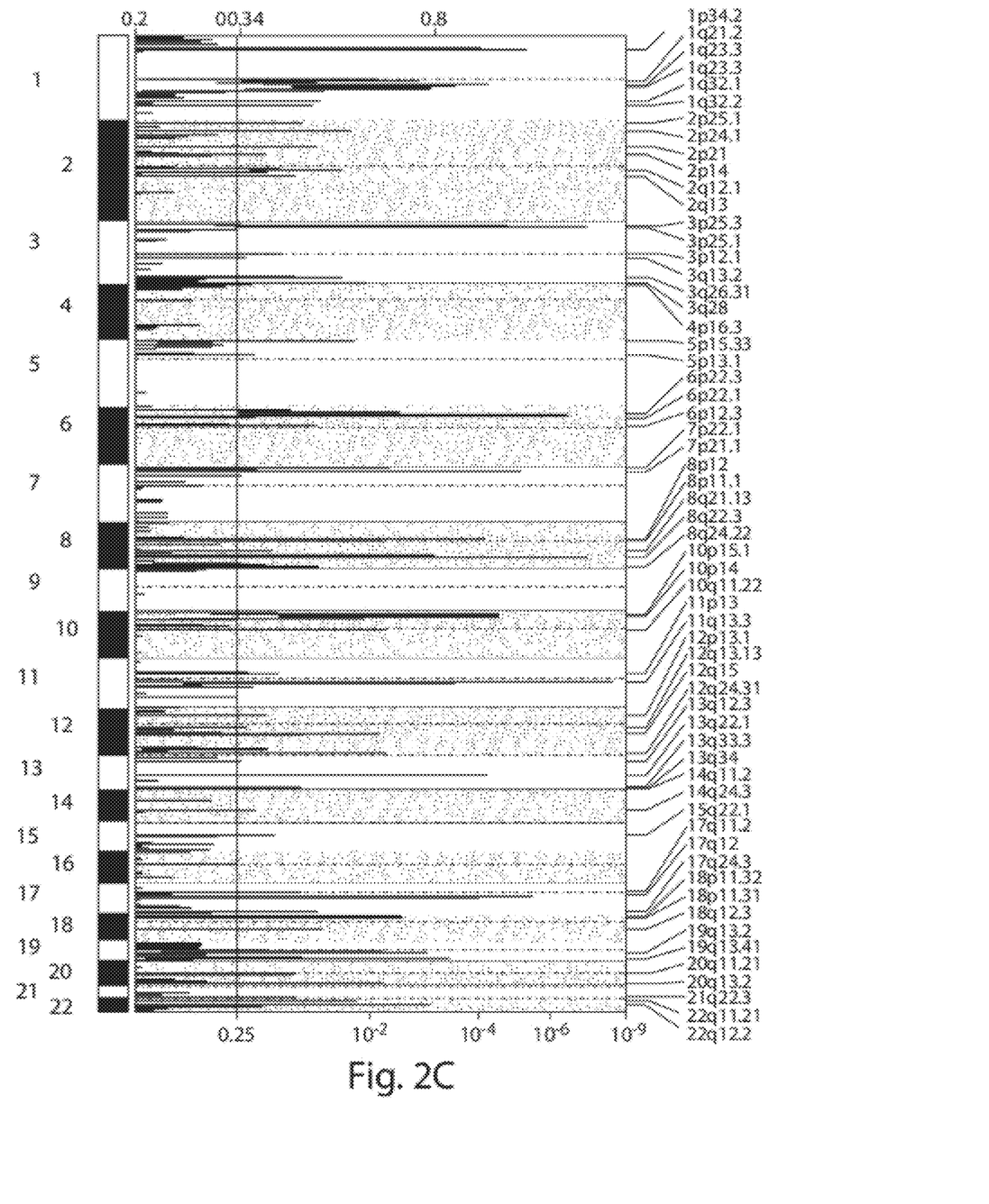
Figure 2D:
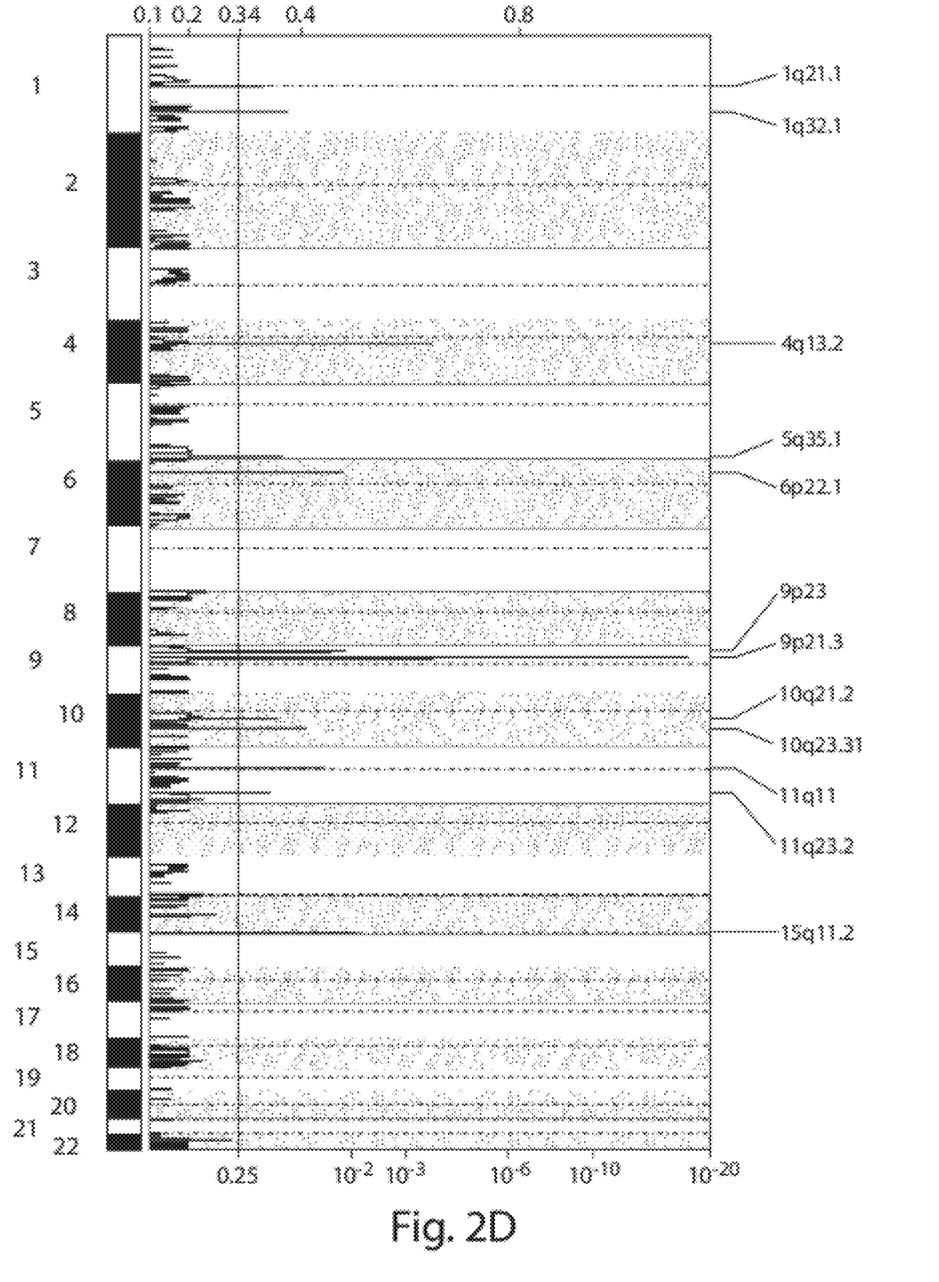

First the GISTIC algorithm was applied to the data to identify regions of recurrent copy number alteration. This approach identified 95 focal and 21 broad (>50% of the chromosome arm) events in the Spanish cohort (FIG. 2A-B) and 91 focal and 16 broad events in the BW/DF cohort (FIG. 2C-D). The results of the broad alteration analysis were largely consistent with the literature, with frequent losses of chromosomes 5q (43%), 8p (69%), 9 (p: 48%; q: 41%), 10q (41%), 11p (49%), 17p (51%), and 22q (40%) and recurrent gains of chromosomes 3q (46%), 5p (48%), 8q (48%), 19q (34%), and 20 (60%). The overlap of the focal amplifications between the cohorts is displayed in Table 4. The most frequent focal loss is 15q11.2 (59%), which was previously reported in aggressive UCs and other histologies but harbors no known tumor suppressor. CDKN2A/B are deleted in 52% of all patients. The tumor suppressor MAP2K4 is the likely target of a focal amplification at 17p11-12, found in 49% of all patients. Also frequently amplified are the SOX4 (50%), ERBB2 (48%) and PPARG (44%) loci. All percentages for both broad and focal events refer to the larger Spanish cohort and GISTIC cutoffs of −0.1 and 0.1.

Figure 3A:
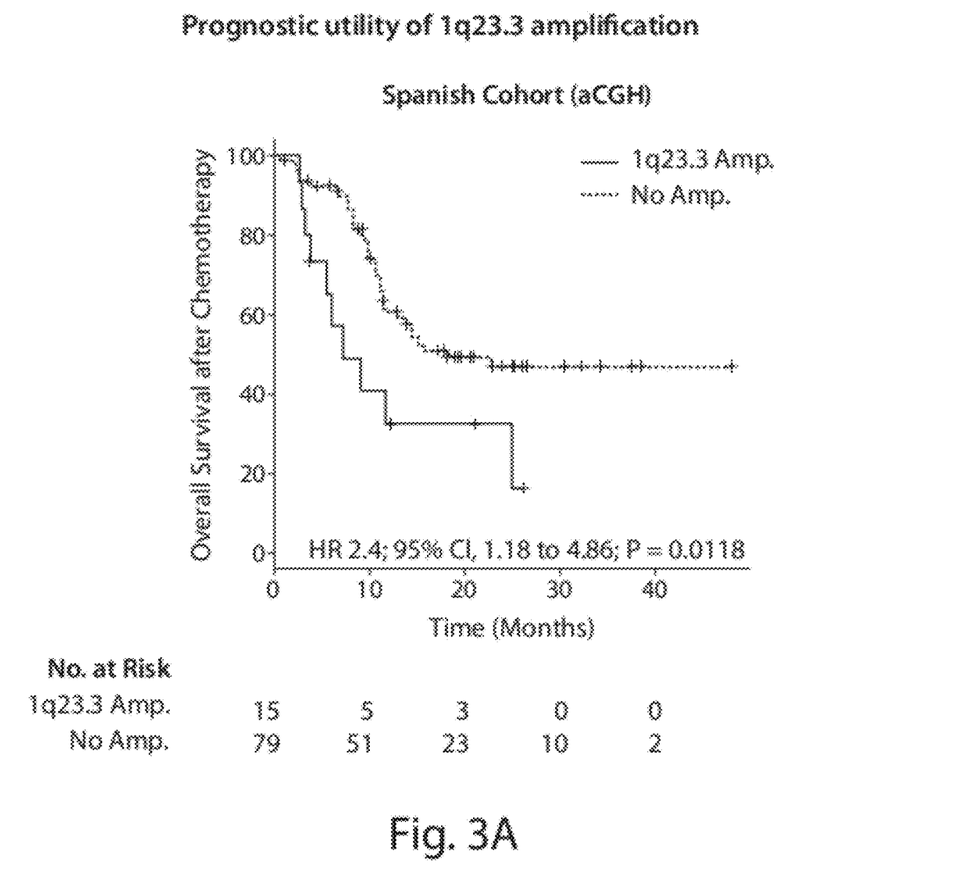
Figure 3B:
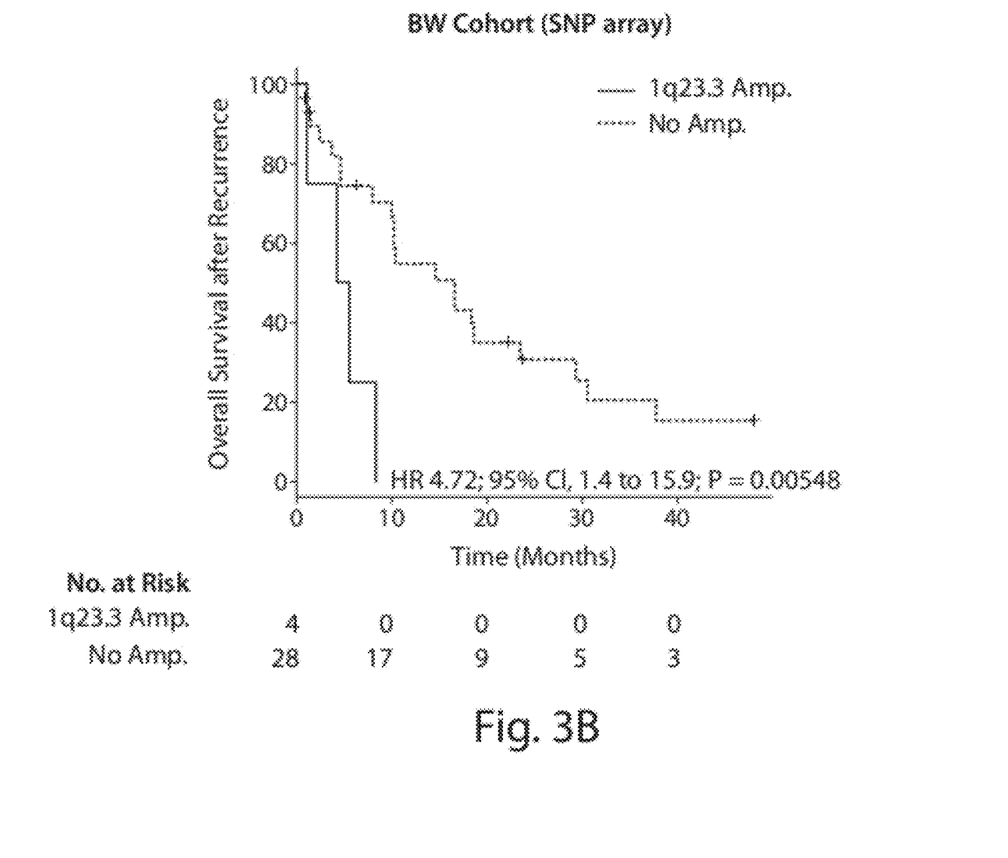
Figure 3C:
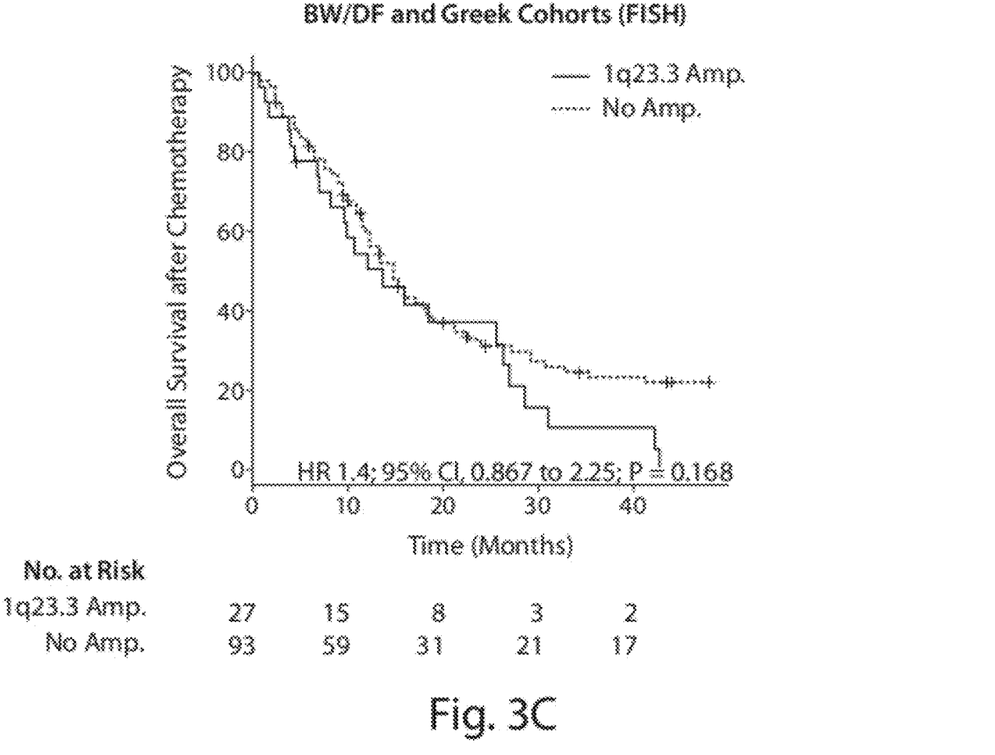
Figure 3D:
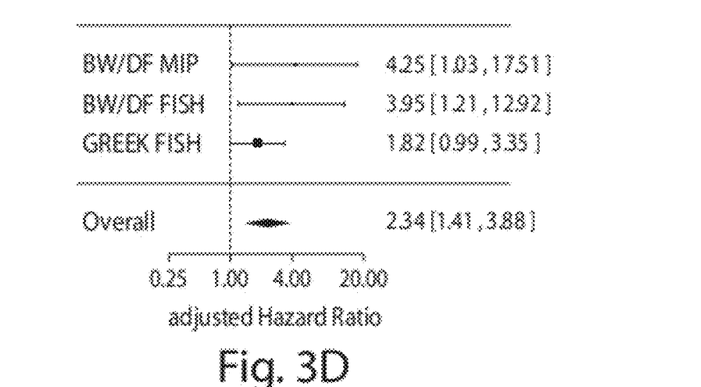

Next, any association of the broad or focal SCNA events with survival in the Spanish cohort was tested. No broad event was found to be significantly associated with overall survival. With regard to focal events, the chromosome bands 1q21.2 and 1q23.3 (chromosome 1:147.645-159.407 Mb) were observed to be significantly associated with overall survival, even after adjusting for ECOG performance status and visceral metastasis (FDR 0.12). The locus 1q23.3 (adjusted Hazard Ratio [HR] 2.96; 95% CI, 1.35 to 6.48; P=0.007) represented the GISTIC peak region with the lowest q-value and largest frequency of high copy number gains among all patients (FIG. 3). This locus was also significantly associated with overall survival after recurrence in the BW/DF validation cohort (n=31; adj. HR 3.73; 95% CI, 1.09 to 12.77; P=0.036). Fluorescence in situ hybridization (FISH) was then performed on subset patients from the Greek and BW/DF cohorts (n=113). After adjusting for ECOG performance status and visceral disease, 1q23.3 amplification, as quantified by FISH, was significantly associated with overall survival (adj. HR 1.71; 95% CI 1.03 to 2.85, P=0.038).

Figure 4:
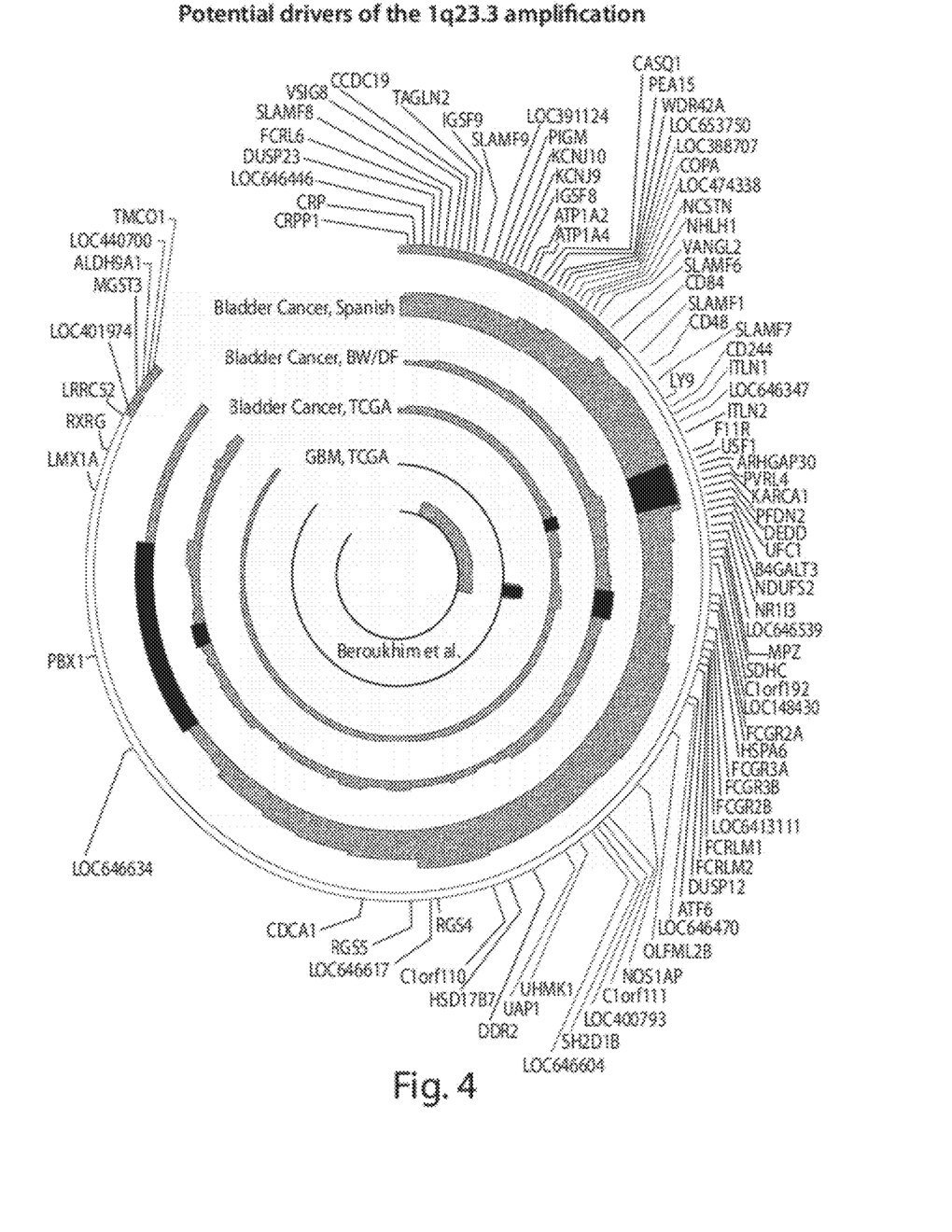
FIG. 4 displays the wide peak amplification regions in three bladder cancer cohorts, in the TCGA primary glioblastoma dataset, as well as the multi-cancer study by Beroukhim et. al. Peak heights visualize the statistical significance (GISTIC q-values). Gene names shown in grey are known cancer genes.

Finally, potential target genes of the 1q23.3 amplification were identified. The GISTIC wide peak regions in the Spanish, BW/DF, and TCGA cohorts were examined. We identified three different peak regions in total, each of which was observed in at least two UC patient cohorts (FIG. 4).

Peak 1, used in the survival analyses, was the highest peak in the Spanish and the TCGA cohorts. This peak harbors, among others, the DEDD gene, over-expression of which has been shown to decrease rates of apoptosis. The second peak contains the FCGR gene cluster, involved in the mediation of immune responses and apoptosis and with frequently reported over-expression as result of 1q23 chromosomal alterations in hematological malignancies. The third peak involves the PBX1 locus, over-expression of which was recently shown to be associated with reduced metastasis-free survival in ERα-positive breast cancer. The FCGR peak was also observed in GBM; similarly, the 1q23.3 locus in general is frequently altered in many cancer types. Peaks 2 and 3 were also tested for association with survival and found to have weaker associations as compared to peak 1.

TABLE 3

Patient Demographics and Characteristics.

| | Spanish | | BW/DF | | Greek | |
|---|---|---|---|---|---|---|
| | N | % | N | % | N | % |
| | 94 | | 47 | | 93 | |
| Pathological stage | | | | | | |
| Stage 0 (Ta) | 10 | 11% | 1 | 2% | | |
| Stage I (T1) | 5 | 5% | 4 | 9% | | |
| Stage II (T2) | 45 | 48% | 7 | 15% | | |
| Stage III (T3, T4) | 28 | 30% | 13 | 28% | | |
| Stage IV (L, M) | 5 | 5% | 13 | 28% | | |
| Missing | 1 | 1% | 9 | 19% | | |
| Visceral disease | | | | | | |
| Yes | 34 | 36% | 29 | 62% | 55 | 59% |
| No | 60 | 64% | 18 | 38% | 31 | 33% |
| Unknown | | | | | 7 | 8% |
| ECOG Performance Status (PS) | | | | | | |
| 0 | 34 | 36% | 29 | 62% | 49 | 53% |
| 1 | 58 | 61% | 5 | 11% | 35 | 38% |
| 2+ | 2 | 2% | 11 | 23% | 2 | 2% |
| Unknown | | | 2 | 4% | 7 | 8% |
| Survival | | | | | | |
| Dead | 46 | 49% | 27 | 96% | 66 | 71% |
| Alive | 48 | 51% | 1 | 4% | 27 | 29% |

TABLE 4

Focal Amplifications. The table shows significant (q-value <0.25) GISTIC focal aberrations in the Spanish and BW/DF cohorts. Multiple peaks in one chromosome band were combined and the average q-value is shown. If known cancer genes were located in the peaks, only these are reported; otherwise, the intersection of the GISTIC target genes in the two cohorts is reported.

| Chr | Type | Freq. (Spanish) | q-value (Spanish) | Freq. (BW/DF) | q-value (BW/DF) | Possible Target Genes |
|---|---|---|---|---|---|---|
| 15q11.2 | Del | 55 (58.5%) | <0.001 | 20 (42.6%) | <0.001 | LOC283755, A26B1, LOC283767 |
| 6p22.3 | Amp | 47 (50%) | <0.001 | 21 (44.7%) | <0.001 | SOX4, CDKAL1 |
| 17q12 | Amp | 45 (47.9%) | <0.001 | 24 (51.1%) | <0.001 | ERBB2 |
| 9p21.3 | Del | 49 (52.1%) | <0.001 | 34 (72.3%) | <0.001 | CDKN2A, CDKN2B |
| 3p25.1 | Amp | 41 (43.6%) | <0.001 | 30 (63.8%) | <0.001 | PPARG |
| 1q23.3 | Amp | 58 (61.7%) | <0.001 | 27 (57.4%) | 0.001 | PBX1, FCGR2B |
| 8q22.3 | Amp | 63 (67%) | <0.001 | 32 (68.1%) | <0.001 | PABPC1, SNX31 |
| 8p12 | Amp | 31 (33%) | <0.001 | 18 (38.3%) | <0.001 | FGFR1, WHSC1L1 |
| 1p34.2 | Amp | 16 (17%) | <0.001 | 23 (48.9%) | <0.001 | MYCL1 |
| 10p14 | Amp | 43 (45.7%) | <0.001 | 23 (48.9%) | 0.002 | GATA3 |
| 14q11.2 | Del | 24 (25.5%) | <0.001 | 20 (42.6%) | 0.018 | OR4N2, OR4K2, A26C2, OR11H12, OR4Q3, OR4M1 |
| 19q13.2 | Amp | 36 (38.3%) | <0.001 | 28 (59.6%) | 0.001 | AKT2 |
| 12q15 | Amp | 26 (27.7%) | <0.001 | 15 (31.9%) | 0.007 | MDM2 |
| 1q21.2 | Amp | 56 (59.6%) | <0.001 | 26 (55.3%) | 0.018 | ARNT |
| 20q11.21 | Amp | 59 (62.8%) | 0.004 | 36 (76.6%) | 0.074 | ASXL1 |
| 6p22.1 | Amp | 42 (44.7%) | 0.005 | 18 (38.3%) | 0.219 | HIST1H1E, HIST1H1T, HIST1H2AE, HIST1H2AD, HIST1H2BD, HIST1H2AC, HIST1H2BG, HIST1H2BF, HIST1H2BE, HIST1H2BC, HIST1H3D, HIST1H4D, HIST1H4E |
| 7p21.1 | Amp | 49 (52.1%) | 0.017 | 26 (55.3%) | <0.001 | AHR |
| 18p11.31 | Amp | 36 (38.3%) | 0.029 | 19 (40.4%) | 0.062 | DLGAP1, FLJ35776 |
| 17q11.2 | Amp | 39 (41.5%) | 0.032 | 18 (38.3%) | 0.183 | SUZ12 |
| 17p11.2 | Del | 46 (48.9%) | 0.033 | 22 (46.8%) | 0.166 | MAP2K4 |
| 5p15.33 | Amp | 38 (40.4%) | 0.037 | 23 (48.9%) | 0.017 | SDHA, SLC9A3, TERT, TRIP13, PDCD6, SLC12A7, TPPP, EXOC3, CEP72, AHRR, BRD9, ZDHHC11, CLPTM1L, NKD2, LOC116349, CCDC127, PLEKHG4B, SLC6A19, SLC6A18, LOC389257 |
| 3p12.1 | Amp | 33 (35.1%) | 0.047 | 15 (31.9%) | 0.110 | VGLL3 |

TABLE 5

Association between 1q23.3 amplification and survival. The table shows the
hazard ratios for 1q23.3 amplification in all cohorts.

| Model | Characteristic | | Hazard Ratio (95% CI) | | |
|---|---|---|---|---|---|
| | | | Spanish cohort (n = 94) | BW/DF cohort (n = 32) | Greek and BW/DF FISH (n = 120) |
| Unadjusted | 1q23.3 Amp | Yes vs No | 2.4 (1.18-4.86) | 4.72 (1.4-15.86) | 1.4 (0.87-2.25) |
| Adjusted | 1q23.3 Amp | Yes vs No | 2.96 (1.35-6.48) | 3.73 (1.09-12.77) | 1.71 (1.03-2.85) |
| | ECOG PS | >1 vs 0 | 1.95 (1-3.81) | 1.93 (0.82-4.55) | 2.38 (1.51-3.75) |
| | visceral disease | Yes vs No | 2.39 (1.26-4.51) | 1.48 (0.65-3.38) | 1.21 (0.77-1.9) |

We claim:

1. A method comprising:
   (i) contacting a nucleic acid isolated from a tumor tissue sample obtained from a subject that has urothelial cell carcinoma with a detectable probe that hybridizes under stringent conditions to one or more genes selected from the group consisting of JAM1, NIT1, PFDN2, PPDX, KAT, USF1, DEDD, UFC1, PVRL4, KLHDC9, and ARHGAP30 to form a nucleic acid—probe hybridization complex;
   (ii) contacting a control nucleic acid with the detectable probe used in (i) to form a control nucleic acid—probe hybridization complex; and
   (iii) measuring the level of formation of the nucleic acid—probe hybridization complex and the level of formation of the control nucleic acid—probe hybridization complex, wherein a copy number gain in the one or more genes exists when the level of formation of the nucleic acid—probe hybridization complex is higher than the level of formation of the control nucleic acid—probe hybridization complex, and
   wherein the control nucleic acid does not have a copy number gain in the one or more genes.

2. The method of claim 1, further comprising extracting nucleic acid from the tumor tissue sample prior to performing the hybridization-based assay.

3. The method of claim 2, wherein the detectable probe is a DNA probe.

4. The method of claim 3, wherein the DNA probe is fluorescently labeled.

5. The method of claim 1, wherein the tumor tissue sample is obtained from a human subject that is known to have invasive or metastatic urothelial carcinoma.

6. The method of claim 1, wherein the isolated nucleic acid is mRNA.

7. The method of claim 1, wherein the isolated nucleic acid is genomic DNA.

8. The method of claim 1, wherein the one or more genes is PFDN2, PPDX, DEDD, or a combination thereof.

9. The method of claim 1, further comprising, prior to step (i), obtaining the tumor tissue sample from the subject that has urothelial carcinoma.

10. A method comprising:
    (i) contacting a nucleic acid isolated from a tumor sample obtained from a subject that has urothelial cell carcinoma with a pair of oligonucleotide primers under conditions to specifically amplify one or more genes selected from the group consisting of JAM1, NIT1, PFDN2, PPDX, KAT, USF1, DEDD, UFC1, PVRL4, KLHDC9, and ARHGAP30 to produce an amplification product;
    (ii) contacting a control nucleic acid with the pair of oligonucleotide primers and under the conditions in (i) to produce a control amplification product; and
    (iii) measuring the amount of the amplification product in the tumor sample and the amount of the control amplification product,
    wherein a copy number gain in the one or more genes exists when the amount of the amplification product in the tumor sample is higher than the amount of the control amplification product, and
    wherein the control sample does not have a copy number gain in the one or more genes.

11. The method of claim 10, wherein the nucleic acid is mRNA.

12. The method of claim 10, wherein the nucleic acid is genomic DNA.

13. The method of claim 10, wherein the one or more genes is PFDN2, PPDX, DEDD, or a combination thereof.

14. The method of claim 10, further comprising, prior to step (i), obtaining the tumor tissue sample from the subject that has urothelial carcinoma.

15. The method of claim 10, further comprising extracting nucleic acid from the tumor tissue sample prior to performing the quantitative amplification-based assay.

16. The method of claim 10, wherein the tumor tissue sample is obtained from a human subject that is known to have invasive or metastatic urothelial carcinoma.

* * * * *

UNITED STATES PATENT AND TRADEMARK OFFICE
CERTIFICATE OF CORRECTION

PATENT NO. : 9,828,643 B2  Page 1 of 1
APPLICATION NO. : 13/475432
DATED : November 28, 2017
INVENTOR(S) : Jonathan E. Rosenberg et al.

It is certified that error appears in the above-identified patent and that said Letters Patent is hereby corrected as shown below:

In the Claims

At Column 15, Line 24 Claim 1 the term "PPDX" should be replaced with the term --PPOX--;
At Column 15, Line 56 Claim 8 the term "PPDX" should be replaced with the term --PPOX--;
At Column 16, Line 26 Claim 10 the term "PPDX" should be replaced with the term --PPOX--;
At Column 16, Line 45 Claim 13 the term "PPDX" should be replaced with the term --PPOX--.

Signed and Sealed this
Thirtieth Day of January, 2018

Joseph Matal
*Performing the Functions and Duties of the
Under Secretary of Commerce for Intellectual Property and
Director of the United States Patent and Trademark Office*